United States Patent [19]
Borcherding et al.

[11] Patent Number: 5,817,661
[45] Date of Patent: Oct. 6, 1998

[54] TRANS CYCLOPENTANYL PURINE ANALOGS USEFUL AS IMMUNOSUPPRESSANTS

[75] Inventors: David R. Borcherding, Loveland, Ohio; Carl K. Edwards, III, Superior, Colo.; Ronald E. Esser, Berkeley Heights, N.J.; Douglas L. Cole, San Diego, Calif.

[73] Assignee: Hoechst Marion Roussel, Inc., Cincinnati, Ohio

[21] Appl. No.: 485,745

[22] Filed: Jun. 7, 1995

Related U.S. Application Data

[63] Continuation-in-part of Ser. No. 369,576, Jan. 6, 1995, abandoned, which is a continuation of Ser. No. 965,601, Nov. 2, 1992, abandoned, which is a continuation-in-part of Ser. No. 804,153, Dec. 6, 1991, abandoned.

[51] Int. Cl.$^6$ .............. C07D 473/34; C07D 473/16; C07D 471/04; A61K 31/52
[52] U.S. Cl. .............. 514/261; 544/254; 544/264; 544/277; 544/280; 546/118; 546/119
[58] Field of Search .............. 514/261; 544/264, 544/277

[56] References Cited

U.S. PATENT DOCUMENTS

| | | | |
|---|---|---|---|
| 3,682,918 | 8/1972 | Druey et al. | 260/256.4 F |
| 3,917,837 | 11/1975 | Lin et al. | 424/253 |
| 4,038,479 | 7/1977 | Elion et al. | 536/24 |
| 4,076,711 | 2/1978 | Ganguly et al. | 424/251 |
| 4,386,093 | 5/1983 | Chiang et al. | 546/118 |
| 4,742,064 | 5/1988 | Vince et al. | 514/258 |
| 4,854,215 | 8/1989 | Shimada et al. | 514/265 |
| 4,859,677 | 8/1989 | Borchardt, et al. | 514/261 |
| 4,916,224 | 4/1990 | Vince et al. | 544/254 |
| 4,954,504 | 9/1990 | Chen et al. | 54/265 |
| 5,039,689 | 8/1991 | Daluge | 514/359 |
| 5,126,452 | 6/1992 | Vince et al. | 514/276 |
| 5,244,896 | 9/1993 | Borcherding et al. | 544/264 |

FOREIGN PATENT DOCUMENTS

| | | |
|---|---|---|
| 0236935 | 9/1987 | European Pat. Off. |
| 0267878 | 5/1988 | European Pat. Off. |
| 0368640 | 5/1990 | European Pat. Off. |
| 0369409 | 5/1990 | European Pat. Off. |
| 0465297 | 1/1992 | European Pat. Off. |
| 0475411 | 3/1992 | European Pat. Off. |
| 2347367 | 11/1977 | France |
| 2714263 | 10/1977 | Germany |

OTHER PUBLICATIONS

Physician's Desk Reference, 47$^{th}$ Edition, (1993) pp. 217, 785–788, 2119–2124.
Silverstein, J. Exp. Med. 173, 357(1991).
Zedeck, Mol. Pharm. 3, 386 (1967).
Trost, et al., A Transition–Metal–Controlled Synthesis of (±) Aristeromycin and (±) 2',3'–diepi–Aristeromycin. An Unusual Directive Effect in Hydroxylations, J. Am. Chem. Soc. vol. 110, 621–622, (1988).
Hasobe, et al., 9(Trans–2'Trans 3'–Dihydroxyclopentanyl)—Adenine and 3–Deazaadenine Analogues of Aristeromycin Which Exhibit Potent Antiviral Activity with Reduced Cytotoxicity. FASEB Journal vol. 4, A1771 (Abstr. #455) (199).
Ault–Riche, et al., Effects of 4'—Modified Analogs of Aristeromycin and Neplanocin A on Metabolism of S–Adenosyl–L–Homocysteine in Mouse L929 Cells, FASEB Journal vol. 4, A2050 (Abstr. #2064) (1990.
Wolf, et al., 4'Modified Analogs of Aristeromycin and Neplacin A: Synthesis and Adenosyl–Homocysteine Hydrolase Inhibitory Activity 199th ACS National Meeting, Boston, Mass., Apr. 1990, Abstrct #27.
Koga, et al., The Synthesis of two 2'Deoxy Carbocyclic Purine Nucleosides Lacking the 5'Methylene, Tetrahedron Letters, vol. 31, 5861, (1990).
Schaffer, et al., Synthesis of Potential Anticancer Agents. XXV Preparation of Some Cis and Trans–2–(6–Substituted 9–Purinyl) cyclopentanols, J. Org. Chem. vol. 25, 771–776, (1960).
Kahan I, Curr. Opin. Immunology 4, 553 (1992).
Kahan II Immunological Reviews #136, p. 29 (1993).

*Primary Examiner*—Mark L. Berch
*Attorney, Agent, or Firm*—T. Helen Payne

[57] ABSTRACT

This invention relates to Trans cyclopentanyl purine analogs of the formula (1)

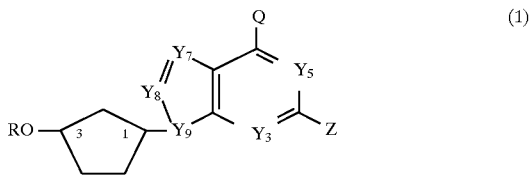

wherein
the substituent in the 3-position on the cyclopentanyl ring is in the Trans configuration relative to the bicyclic substituent,
$Y_3$, $Y_5$, $Y_7$, $Y_9$ are each nitrogen and $Y_8$ is a CH group,
R is a hydrogen, a $C_1$–$C_7$ alkyl acyl or aryl acyl,
Q is $NH_2$, halogen or hydrogen,
Z is hydrogen, halogen, or $NH_2$;
or a pharmaceutically-acceptable salt thereof, and to their use as immunosuppressants.

19 Claims, No Drawings

TRANS CYCLOPENTANYL PURINE ANALOGS USEFUL AS IMMUNOSUPPRESSANTS

This application is a continuation-in-part of application Ser. No. 08/369,576, filed Jan. 6, 1995, abandoned which is a continuation of application Ser. No. 07/965,601, filed Nov. 2, 1992, now abandoned, which is a continuation-in-part of application Ser. No. 07/804,153, filed Dec. 6, 1991, now abandoned.

FIELD OF THE INVENTION

This invention relates to certain Trans cyclopentanyl purine analogs which are useful as immunosuppressants.

BACKGROUND OF THE INVENTION

Immunity is concerned with the recognition and disposal of foreign antigenic material which is present in the body. Typically the antigens are in the form of particulate matter (i.e., cells, bacteria, etc.) or large protein or polysaccharide molecules which are recognized by the immune system as being "non-self", i.e., detectably different or foreign from the animals own constituents. Potential antigens can be a variety of substances, often proteins, which are most frequently located on the outer surfaces of cells. For example, potential antigens can be found on pollen grains, tissue grafts, animal parasites, viruses, and bacteria. Once the antigenic material is recognized as "non-self" by the immune system, natural (non-specific) and/or adaptive immune responses can be initiated and maintained by the action of specific immune cells, antibodies and the complement system. Under certain conditions, including in certain disease states, an animal's immune system will recognize its own constituents as "non-self" and initiate an immune response against "self" material.

An immune response can be carried out by the immune system by means of natural or adaptive mechanisms, each of which are composed of both cell-mediated and humoral elements. Natural mechanisms for immune response refer to those mechanisms involved in essentially non-specific immune reactions which involve the complement system and myeloid cells alone, such as macrophages, mast cells and polymorphonuclear leukocytes (PMN), in reacting to certain bacteria, viruses, tissue damage and other antigens. These natural mechanisms provide what is referred to as natural immunity. Adaptive mechanisms for immune response refer to those mechanisms which are mediated by lymphocytes (T and B cells) and antibodies which can respond selectively to thousands of different materials recognized as "non-self". These adaptive mechanisms provide what is referred to as adaptive immunity and lead to a specific memory and a permanently altered pattern of response in adaptation to the animal's own environment. Adaptive immunity can be provided by the lymphocytes and antibodies alone or, more commonly, can be provided by the interaction of lymphocytes and antibodies with the complement system and myeloid cells of the natural mechanisms of immunity. The antibodies provide the humoral element of the adaptive immune response and the T-cells provide the cell-mediated element of the adaptive immune response.

Natural mechanisms of immune response involve phagocytosis by macrophages and PMN whereby foreign material or antigen is engulfed and disposed of by these cells. In addition, macrophages can kill some foreign cells through its cytotoxic effects. The complement system which is also involved in natural immunity is made up of various peptides and enzymes which can attach to foreign material or antigen and thereby promote phagocytosis by macrophages and PMN, or enable cell lysis or inflammatory effects to take place.

Adaptive mechanisms of immune response involve the actions against specific antigens of antibody secreted by B-lymphocytes (or B-cells) as well as the actions of various T-lymphocytes (or T-cells) on a specific antigen, on B-cells, on other T-cells and on macrophages.

Antibodies, which are responsible for the humoral aspect of adaptive immunity, are serum globulins secreted by B-cells with a wide range of specificity for different antigens. Antibodies are secreted in response to the recognition of specific antigens and provide a variety of protective responses. Antibodies can bind to and neutralize bacterial toxins and can bind to the surface of viruses, bacteria, or other cells recognized as "non-self" and thus promote phagocytosis by PMN and macrophages. In addition, antibodies can activate the complement system which further augments the immune response against the specific antigen.

Lymphocytes are small cells found in the blood which circulate from the blood, through the tissues, and back to the blood via the lymph system. There are two major subpopulations of lymphocytes called B-cells and T-cells. B-cells and T-cells are both derived from the same lymphoid stem cell with the B-cells differentiating in the bone marrow and the T-cells differentiating in the thymus. The lymphocytes possess certain restricted receptors which permit each cell to respond to a specific antigen. This provides the basis for the specificity of the adaptive immune response. In addition, lymphocytes have a relatively long lifespan and have the ability to proliferate clonally upon receiving the proper signal. This property provides the basis for the memory aspect of the adaptive immune response.

B-cells are the lymphocytes responsible for the humoral aspect of adaptive immunity. In response to recognition of a specific foreign antigen, a B-cell will secrete a specific antibody which binds to that specific antigen. The antibody neutralizes the antigen, in the case of toxins, or promotes phagocytosis, in the case of other antigens. Antibodies also are involved in the activation of the complement system which further escalates the immune response toward the invading antigen.

T-cells are the lymphocytes responsible for the cell-mediated aspect of adaptive immunity. There are three major types of T-cells, i.e., the Cytotoxic T-cells, Helper T-cells and the Suppressor T-cells. The Cytotoxic T-cells detects and destroys cells infected with a specific virus antigen. Helper T-cells have a variety of regulatory functions. Helper T-cells, upon identification of a specific antigen, can promote or enhance an antibody response to the antigen by the appropriate B-cell and it can promote or enhance phagocytosis of the antigen by macrophages. Suppressor T-cells have the effect of suppressing an immune response directed toward a particular antigen.

The cell-mediated immune response is controlled and monitored by the T-cells through a variety of regulatory messenger compounds secreted by the myeloid cells and the lymphocyte cells. Through the secretion of these regulatory messenger compounds, the T-cells can regulate the proliferation and activation of other immune cells such as B-cells, macrophages, PMN and other T-cells. For example, upon binding a foreign antigen, a macrophage or other antigen presenting cell can secrete interleukin-1 (IL-1) which activates the Helper T-cells. T-cells in turn secrete certain lymphokines, including interleukin-2 (IL-2) and γ-interferon, each of which have a variety of regulatory effects in the cell-mediated immune response. Lymphokines are a large family of molecules produced by T-cells (and sometimes B-cells) including IL-2, which promotes the clonal proliferation of T-cells;

MAF or macrophage activation factor, which increases many macrophage functions including phagocytosis, intracellular killing and secretion of various cytotoxic factors;

NAF or neutrophil activation factor, which increases many functions of the PMN including phagocytosis, oxygen radical production, bacterial killing, enhanced chemotaxis and enhanced cytokine production;

MIF or macrophage migration factor, which by restricting the movement of macrophages, concentrates them in the vicinity of the T-cell;

γ-interferon, which is produced by the activated T-cell and is capable of producing a wide range of effects on many cells including inhibition of virus replication, induction of expression of class II histocompatibility molecules allowing these cells to become active in antigen binding and presentation, activation of macrophages, inhibition of cell growth, induction of differentiation of a number of myeloid cell lines.

Activated macrophages and PMNs, which provide an enhanced immune response as part of the cell-mediated adaptive immunity, are characterized as having increased production of reactive oxygen intermediates. This increased production of reactive oxygen intermediates, or respiratory burst, is known as "priming". Certain lymphokines, such as γ-interferon, trigger this respiratory burst of reactive oxygen intermediates in macrophages and PMNs. Thus, lymphokines, such as y-interferon, which are secreted by the T-cells provide an activation of these macrophages and PMNs which results in an enhanced cell-mediated immune response.

The immune response can provide an immediate or a delayed type of response. Delayed-type hypersensitivity is an inflammatory reaction which occurs in immune reactive patients within 24–48 hours after challenge with antigen and is the result primarily of a cell-mediated immune response. In contrast, immediate-type hypersensitivity, such as that seen in anaphylactic or Arthus reactions, is an inflammatory reaction which occurs in immune reactive patients within minutes to a few hours after challenge with antigen and is the result primarily of humoral or antibody-mediated immune response.

The ability of the immune system, and in particular the cell-mediated immune system, to discriminate between "self" and "non-self" antigens is vital to the functioning of the immune system as a specific defense against invading microorganisms. "Non-self" antigens are those antigens or substances in the body which are detectably different or foreign from the animals own constituents. "Self" antigens are those antigens which are not detectably different or foreign from the animals own constituents. Although the immune response is a major defense against foreign substances which can cause disease, it cannot distinguish between helpful and harmful foreign substances and destroys both.

There are certain situations, such as with an allogeneic transplant or in "graft versus host" disease, where it would be extremely useful to suppress the immune response in order to prevent the rejection of helpful foreign tissue or organs. Allogeneic tissues and organs are tissues and organs from a genetically different member of the same species. "Graft versus host" disease occurs where the transplanted tissue, for example in a bone marrow transplant, contains allogeneic T-cells of the donor which cause an immune response against the recipient's own tissues. Although both humoral and cell-mediated immune responses play a role in the rejection of allogeneic tissues and organs, the primary mechanism involved is the cell-mediated immune response. Suppression of the immune response, and in particular, suppression of cell-mediated immune response, would thus be useful in preventing such rejection of allograft tissues and organs. For example, cyclosporin A is currently used as an immunosuppressive agent in the treatment of patients receiving allogeneic transplants and in "graft versus host" disease.

There are times when the individual's immunological response causes more damage or discomfort than the invading microbes or foreign material, as in the case of allergic reactions. Suppression of the immune response in these cases would be desirable.

Occasionally, the immunological mechanisms become sensitized to some part of the individual's own body causing interference with or even destruction of that part. The ability to distinguish between "self" and "not self" is impaired and the body begins to destroy itself. This can result in an autoimmune diseases such as rheumatoid arthritis, insulin-dependent diabetes mellitus (which involves the autoimmune destruction of the β-cells of the islets of Langerhans which are responsible for the secretion of insulin), certain hemolytic anemias, rheumatic fever, thyroiditis, ulceractive colitis, myestheniagravis, glomerulonephritis, allergic encephalo-myelitis, continuing nerve and liver destruction which sometimes follows viral hepatitis, multiple sclerosis and systemic lupus erythematosus. Some forms of autoimmunity come about as the result of trauma to an area usually not exposed to lymphocytes such as neural tissue or the lens of the eye. When the tissues in these areas become exposed to lymphocytes, their surface proteins can act as antigens and trigger the production of antibodies and cellular immune responses which then begin to destroy those tissues. Other autoimmune diseases develop after exposure of the individual to antigens which are antigenically similar to, that is cross-react with, the individual's own tissue. Rheumatic fever is an example of this type of disease in which the antigen of the streptococcal bacterium which causes rheumatic fever is cross-reactive with parts of the human heart. The antibodies cannot differentiate between the bacterial antigens and the heart muscle antigens and cells with either of those antigens can be destroyed. Suppression of the immune system in these autoimmune diseases would be useful in minimizing or eliminating the effects of the disease. Certain of these autoimmune diseases, for example, insulin-dependent diabetes mellitus, multiple sclerosis and rheumatoid arthritis, are characterized as being the result of a cell-mediated autoimmune response and appear to be due to the action of T-cells [See Sinha et al. *Science* 248, 1380 (1990)]. Others, such as myestheniagravis and systemic lupus erythematosus, are characterized as being the result of a humoral autoimmune response [Id.].

Suppression of the immune response would thus be useful in the treatment of patients suffering from autoimmune diseases. More particularly, suppression of cell-mediated immune response would thus be useful in the treatment of patients suffering from autoimmune diseases due to the action of T-cells such as insulin-dependent diabetes mellitus, multiple sclerosis and rheumatoid arthritis. Suppression of humoral immune response would be useful in the treatment of patients suffering from T-cell independent autoimmune diseases such as myestheniagravis and systemic lupus erythematosus.

SUMMARY OF THE INVENTION

The present invention provides novel compounds of the formula (1)

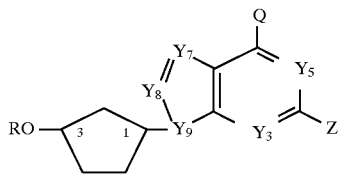

wherein
- the substituent in the three position on the cyclopentanyl ring is in the TRANS configuration relative to the bicyclic substituent,
- $Y_3$, $Y_5$, $Y_7$, $Y_9$ are each independently nitrogen or a CH group,
- R is hydrogen, $C_1$–$C_7$ alky acyl or aryl acyl,
- Q is $NH_2$, halogen or hydrogen, and
- Z is hydrogen, halogen, or $NH_2$;

or a pharmaceutically-acceptable salt thereof.

The present invention also provides a method of effecting immunosuppression, and more specifically, a method of suppressing adaptive immunity, in a patient in need thereof comprising administering to said patient an effective immunosuppressive amount of a compound of formula (1).

In addition, the present invention provides a pharmaceutical composition comprising an effective immunosuppressive amount of a compound of formula (1) in admixture or otherwise in association with one or more pharmaceutically acceptable carriers or excipients.

DETAILED DESCRIPTION OF THE INVENTION

As used herein the term "halogen" refers to monovalent iodine, bromine, chlorine or fluorine radicals, the term "nitrogen" refers to a trivalent nitrogen radical and the term "CH group" refers to a methylidyne radical.

As used herein, the term $C_1$–$C_7$ alkyl acyl is composed of an acyl substituent combined with a $C_1$–$C_7$ alkyl substituent. The term acyl refers to a radical of a carboxylic acid created by the removal of the hydroxide from the carboxy group [—C(O)—]. The term $C_1$–$C_7$ alkyl refers to the hydrocarbon radical which may be derived from an alkane having from 1 to 7 carbon atoms in a straight chain or branched chain configuration. The combination of a $C_1$–$C_7$ alkyl radical with the acyl radical results in the $C_1$–$C_7$ alkyl acyl term. Included within the scope of the term $C_1$–$C_7$ alkyl acyl are the methyl acyl $CH_3$—C(O)—, ethyl acyl $CH_3CH_2$—C(O)—, n-propyl acyl $CH_3CH_2CH_2$—C(O)—, isopropyl acyl $(CH_3)_2CH$—C(O)—, n-butyl acyl $CH_3(CH_2)$—C(O)—, sec. butyl acyl $CH_3CH_2CH(CH_3)$—C(O)—, and the like.

The aryl acyl term refers to the radical composed of an acyl substituent and an aryl substituent. The term acyl refers to a radical of a carboxylic acid created by the removal of a hydroxide ion from the carboxyl group [C(O)—]. The term aryl refers to the group that remains after the conceptual removal of a hydrogen from a ring position of a benzene or a substituted benzene nucleus or a nicotinoyl. The benzene nucleus may be optionally substituted with up to three substituents selected from the groups consisting of Cl,Br,F, I,$C_1$–$C_4$ alkyl, $NH_2$, or OH. Included within the scope of this term are benzoyl $C_6H_5$—C(O)—, p-chlorobenzoyl $C_6H_4Cl$—C(O)—, 4-fluorobenzoyl $C_6H_4F$—C(O)—, o-toluyl $CH_3C_6H_4$—C(O)—, nicotinoyl $C_5H_4N$—C(O)—, and the like.

As used herein, the term "$C_1$–$C_4$ alkyl" refers to a saturated straight or branched chain hydrocarbyl radical of one to four carbon atoms and includes methyl, ethyl, propyl, isopropyl, tertiary butyl, and the like.

As used herein, the term "pharmaceutically-acceptable salts" refers to acid addition salts of the compounds of formula (1) wherein the toxicity of the compound is not increased compared to the non-salt. Representative examples of pharmaceutically-acceptable salts, which are made by treating the compounds of formula (1) with the corresponding acids, are: hydrobromide, hydrochloride, sulfuric, phosphoric, nitric, formic acetic propionic, succinic, glycolic, lactic, malic, tartaric, citric ascorbic, α-ketoglutaric, glutamic, aspartic, maleic, hydroxymaleic, pyruvic, phenylacetic, benzoic, para-aminobenzoic, anthranilic, para-hydroxybenzoic, salicylic, para-aminosalicylic, methanesulfonic, ethanesulfonic, hydroxyethanesulfonic, ethylenesulfonic, halobenzenesulfonic, toluenesulfonic, naphthalenesulfonic and sulfanilic acids. The hydrochloride is preferred as the pharmaceutically-acceptable salt of compounds of formula (1).

It is understood that the substituents on the cyclopentanyl ring of the compounds of formula (1) have a TRANS configuration relative to the bicyclic substituent. It is further understood that the compounds of formula (1) may exist in stereoisomeric configurations. The compounds of formula (1) encompass and include both the individual stereoisomers and racemic mixtures.

A general synthetic procedure for preparing compounds of formula (1) wherein $Y_9$ is nitrogen is set forth in Scheme A.

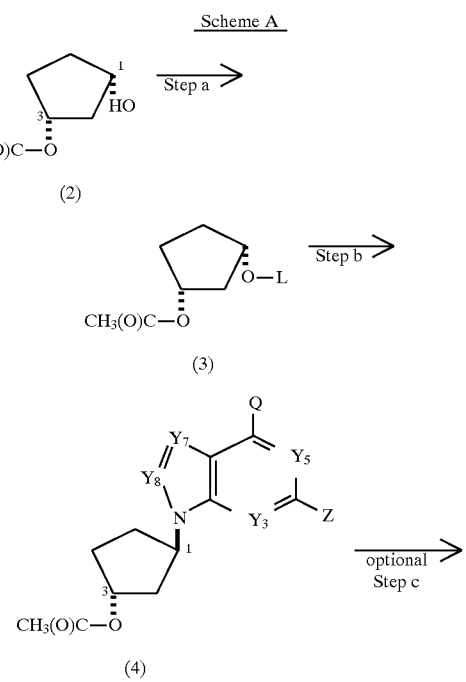

-continued
Scheme A

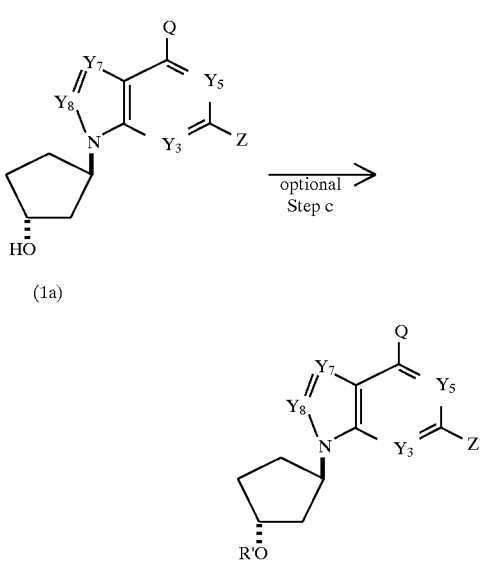

L = Leaving group
R' = C$_1$–C$_8$ alkyl acyl or aryl acyl

The 1-hydroxy of cis-3-acetoxycyclopentan-1-ol is derivatized with a suitable leaving group (L) in step a of Scheme A. The particular leaving group can be one of many which are well known and appreciated in the art. Representative examples of suitable leaving groups are brosyl, tosyl, mesylate. The preferred leaving group for step a is the mesylate.

In step b the leaving group of the cyclopentane derivative formed in step a is displaced with the desired nucleoside base, forming the trans-carbocyclic nucleoside analog. The preferred base for step b is adenine. When the 3-acetoxy analog is desired, the product of step b may be isolated or converted to the appropriate salt using procedures well known and appreciated in the art.

In step c the acetoxy group may be hydrolyzed with a base such a potassium carbonate to an alcohol according to procedures which are well known and appreciated in the art. When the 3-hydroxy analog is preferred, the product of this reaction may be isolated or converted to the appropriate salt using procedures well known and appreciated in the art.

In step d the 3-hydroxyl group may be converted to other alkyl acyl or aryl acyl (R') analogs by techniques which are well known and appreciated in the art. For example if the benzoyl derivative is desired, the 3-hydroxy carbocyclic nucleoside can be reacted with benzoyl chloride in the presence of base to form the 3-benzoyl analogue.

The following example presents a typical synthesis as described by Scheme A. This example is understood to be illustrative only and is not intended to limit the scope of the invention in any way. The following terms have the indicated meaning: "g" refers to grams; "mmol" refers to millimoles; ml refers to milliters; "DMF" refers to dimethylformamide; "°C." refers to degrees Celsius; "mg" refers to milligrams; "N" refers to normality; "pH" refers to the negative log of the hydronium ion.

EXAMPLE 1

(1R,3R)-TRANS-1(9-ADENYL)CYCLOPENTAN-3-OL HYDROCHLORIDE

Step a: (1S,3R)-Cis-1-Methanesulfonyloxy-3-acetoxycyclopentane

Add triethylamine dropwise (1.21 g, 12.0 mmol) to a stirring solution of (1S,3R)-cis-3-acetoxycyclopentan-1-ol (1.44 g, 10.0 mmol) and methanesulfonyl chloride (1.29 g, 11.0 mmol) in 20 ml of methylene chloride at 0° C. Remove the ice bath after the addition is complete. Stir the solution for 20 minutes at room temperature, then, extract the solution with water(30 ml) and brine (30 ml). Dry over sodium sulfate and concentrate the solution to give a yellow oil; 2.1 g of product (94% yield). Use this product immediately in the next reaction without further purification. $^1$H NMR (CDCL$_3$,TMS); 5.09(m,2H), 2.98(s,3H), 2.4,1.9 (m,9H).

Step b: (1R,3R)-Trans-1-(9-Adenyl)-3-acetoxycyclopentane

To a stirring suspension of adenine (4.1 g, 30.0 mmol) in DMF (50 ml), add sodium hydride (60%,1.0 g, 30.0 mmol). Heat the mixture at 55° C. for two hours. Add a solution of (1S,3R)-cis-1-methanesulfonyloxy-3-acetoxycyclopentane (2.0 g, 9.1 mmol) in 20 ml of DMF to the solution and allow to stir for 24 to 48 hours at 55° C. Filter the solution then evaporate the DMF. Take the residue up in 100 ml of methylene chloride. Extract with water (2×200 ml) and brine (20 ml). Dry the solution with sodium sulfate and concentrate to dryness. Take up the residue in methylene chloride then apply to a 40 g silica gel column. Elute the product with 9:1 methylene chloride/ethanol. Collect the fraction containing the product and concentrate to dryness; 1.32 g of product (56% yield). UV(MEOH; 261.5 nm); [α]$_{365}$=29.40 (c 1.7 mg./ml,MeOH); $^1$H-NMR(CDCL3, TMS)=8.35(s,1H), 7.82 (s,1H), 5.41(m,1H), 5.09 (m,1H), 2.55–1.8 (m,9H).

Step c: (1R,3R)-Trans-1-(9-Adenyl)-3-hydroxycyclopentane

Add (1R,3R)-trans-1(9-adenyl)-3-acetoxycyclopentane (600 mg. 2.26 mmol.) and potassium carbonate (500 mg, 3.6 mmol.) to a solution of 25 ml of methanol and 5 ml of water. Stir the mixture at room temperature for 20 minutes. Remove the solid potassium carbonate by filtration and concentrate the filtrate to dryness. Take the residue up in ethanol (with 10% methanol), then allow to stand at room temperature for 30 minutes and remove the precipitate which forms by filtration. Adjust the pH of the filtrate to pH 3 with 6N HCL and concentrate to dryness. Redissolve the material in water and lypholyze to a white powder; (540 mg, 93% yield). UV (MeOH; 261 nm); [α]$_{365}$=−40.0° (c 0.6 mg/ml, MeOH); $^1$H NMR (DMSO-d6, TMS) 8.20(s,1H), 8.17 (s,1H), 5.11 (m,1H), 4.44 (m,1H), 2.4–2.1 (m,4H), 2.0 (m,1H), 1.7 (m,1H).

In general, where it is desired to synthesize the corresponding (1S,3S) enantiomer of the compounds of formula (1), procedures similar to those described above may be followed using the appropriate starting materials. The following example presents a typical synthesis as described by Scheme A. This example is understood to be illustrative only and is not intended to limit the scope of the invention in any way.

EXAMPLE 2

(1S,3S)-TRANS-1(9-ADENYL)CYCLOPENTAN-3-OL HYDROCHLORIDE

Step a: (1R,3S)-Cis-1-Methanesulfonyloxy-3-acetoxycyclopentane

Add triethylamine dropwise (1.21 g, 12.0 mmol) to a stirring solution of (1R,3S)-cis-3-acetoxycyclopentan-1-ol (1.44 g, 10.0 mmol) and methanesulfonyl chloride (1.29 g, 11.0 mmol) in 20 ml of methylene chloride at 0° C. Remove the ice bath after the addition is complete. Stir the solution for 20 minutes at room temperature, then, extract the solution with water(30 ml) and brine (30 ml). Dry over sodium sulfate and concentrate the solution to give a yellow oil; 2.1 g of product (94% yield). Use this product immediately in the next reaction without further purification. $^1$H NMR (CDCL$_3$,TMS); 5.09(m,2H), 2.98(s,3H), 2.4,1.9 (m,9H).

Step b: (1S,3S)-Trans-1-(9-Adenyl)-3-acetoxycyclopentane

To a stirring suspension of adenine (4.1 g, 30.0 mmol) in DMF (50 ml), add sodium hydride (60%,1.0 g, 30.0 mmol). Heat the mixture at 55° C. for two hours. Add a solution of (1R,3S)-cis-1-methanesulfonyloxy-3-acetoxycyclopentane (2.0 g, 9.1 mmol) in 20 ml of DMF to the solution and allow to stir for 24 to 48 hours at 55° C. Filter the solution then evaporate the DMF. Take the residue up in 100 ml of methylene chloride. Extract with water (2×200 ml) and brine (20 ml). Dry the solution with sodium sulfate and concentrate to dryness. Take up the residue in methylene chloride then apply to a 40 g silica gel column. Elute the product with 9:1 methylene chloride/ethanol. Collect the fraction containing the product and concentrate to dryness; 1.2 g of product (46% yield). UV(MEOH; 261.5 nm); $[\alpha]_{365}$=+29.4 (c 1.7 mg./ml,MeOH); 1H-NMR(CDCL3, TMS)=8.34(s,1H), 7.82 (s,1H), 5.41(m,1H), 5.09 (p,1H), 2.5–1.8 (m,9H).

Step c: (1S,3S)-Trans-1-(9-Adenyl)-3-hydroxycyclopentane

Add (1S,3S)-trans-1(9-adenyl)-3-acetoxycyclopentane (1.2 g 4.6 mmol.) and potassium carbonate (1.0 g, 7.2 mmol.) to a solution of 25 ml of methanol and 5 ml of water. Stir the mixture at room temperature for 20 minutes. Remove the solid potassium carbonate by filtration and concentrate the filtrate to dryness. Take the residue up in ethanol (with 10% methanol), then allow to stand at room temperature for 30 minutes and remove the precipitate which forms by filtration and concentrate to dryness. Take up the residue in methylene chloride, then apply to a 75 g silica gel column. Elute the product with 9:1 methylene chloride/ ethanol. Collect the fraction containing the product and concentrate to dryness. Add H$_2$O and adjust the pH to 3 with 6N HCL and concentrate to dryness. Redissolve the material in water and lypholyze to a white powder; (900 mg, 76% yield). UV (MeOH; 261 nm); $[\alpha]_{365}$=+40.0° (c 0.6 mg/ml, MeOH); 1H NMR (DMSO-d6, TMS) 8.20(s,1H), 8.17 (s,1H), 5.11 (p,1H), 4.44 (m,1H), 2.4–2.1 (m,4H), 2.0 (m,1H), 1.7 (m,1H).

EXAMPLE 3

(1R,3R)-TRANS-1-[9-(2,6-DIAMINO)PURINE] CYCLOPENTAN-3-OL

Step b: (1R,3R)-Trans-1-[9-(2,6-diamino)purine]-3-acetoxycyclopentane

To a stirring suspension of 2,6-diaminopurine sulfate (15.96 g, 60.0 mmol) in 150 mL of DMF is added sodium hydride (60%, 5.79 g, 180.0 mmol), and the moisture is then heated at 55° C. for two hours. A solution of (1S,3R)-cis-1-methanesulfonyloxy-3-acetoxy-cyclopentane (4.44 g, 20.0 mmol) in 50 mL DMF is added to the solution and allowed to stir for 48 hours at 60° C. The DMF is then removed and the residue is taken up in 100 mL of methylene chloride and extracted with water and brine. The solution if dried with sodium sulfate, then concentrated to dryness, and the residue is taken up in methylene chloride and applied to a silica gel column and the product is eluted with 9:1 methylene chloride/ethanol. The fraction containing the product is collected and concentrated to dryness to give 2.3 g of product (42% yield).$[\alpha]_{589}$=+9.1° (c 0.002, MeoH); $^1$H-NMR (CDCl$_3$, TMS) 7.88 (s, 1H), 7.74 (s, 2H, exD$_2$O), 5.85 (s, 2H, exD$_2$O), 5.31 (m, 1H), 4.89 (p, 1H), 2.5–1.8 (m, 9H).

Step c: (1R,3R)-trans-1-[9-(2,6-diamino)purine] cyclopentan-3-ol

The (1R,3R)-trans-1-[9-(2,6-diamino)purine]-3-acetoxycyclopentane (1.8 g, 6.5 mmol) and potassium carbonate (2.6 g, 9.1 mmol) is added to 250 mL of methanol and 5 mL of water, and solid potassium carbonate is removed by filtration, and the filtrate is concentrated to dryness. The solid is purified on silica gel using methylene chloride/methanol (4:1) to give 1.3 g of product (86% yield). UV (EtOH; 257 nm and 283 nm);$[\alpha]_{365}$=−16.7° (c 0.002, MeoH); $^1$H-NMR (DMSO-d$_6$, TMS) 7.79 (s, 1H), 6.56 (s, 2H, exD$_2$O), 5.76 (s, 2H, exD$_2$O), 4.86 (p, 1H), 4.7 (br. s, 1H, exD$_2$O), 4.34 (m, 1H), 2.3–1.8 (m, 5H), 1.56 (m, 1H).

The following compounds can be prepared by procedures analogous to those described above for Example 1 using readily available starting materials. The stereo configuration may be (1R,3R) or (1S,3S) or a racemic mixture of these configurations:

Trans-1-[9-(3-deazaadenyl)]-3-hydroxycyclopentane hydrochloride

Trans-1-[9-(7-deazaadenyl)]-3-hydroxycyclopentane hydrochloride

Trans-1-[9-purinyl)-3-hydroxycyclopentane hydrochloride

Trans-1-[9-(8-azaadenyl)]-3-hydroxycyclopentane hydrochloride

Trans-1-[9-(2-aminopurinyl)]-3-hydroxycyclopentane hydrochloride

Trans-1-[9-(2-amino-6-chloropurinyl)]-3-hydroxycyclopentane hydrochloride.

Trans-1-[9-(6-chloropurinyl)]-3-hydroxycyclopentane hydrochloride.

The starting materials for the synthetic scheme described above, including (1S,3R)-Cis-3-acetoxycyclopentan-1-ol, adenine, 7-deazaadenine, purine, 8-azaadenine, 2-aminopurine, 2,6-diaminopurine and 2-amino-6-chloropurine, are readily available or can be made according to conventional procedures and techniques well known and appreciated in the art.

The stereochemistry of the final product is controlled by the selection of a starting material with the appropriate configuration.

A general synthesis procedure for preparing compounds of formula (1) where $Y_8$ and $Y_9$ are each a CH group is presented in Scheme B.

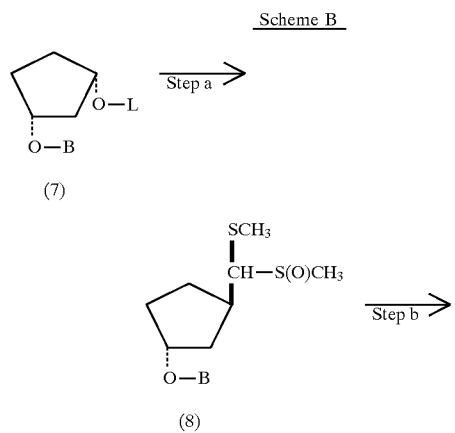

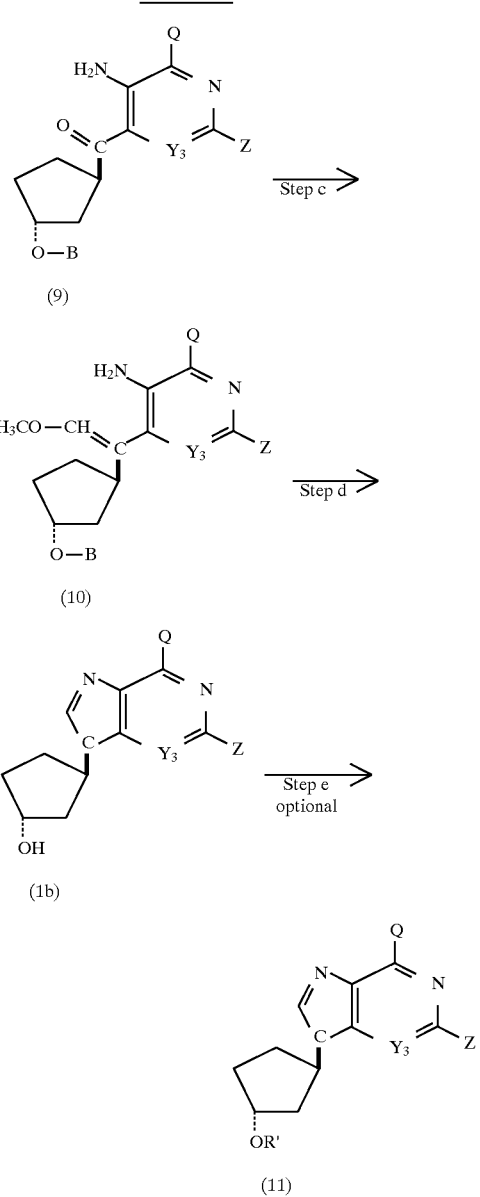

B = Blocking group
R' = C₁–C₈ alkyl acyl or aryl acyl

In step a, the cyclopentane derivative (7) is reacted with the sodium anion of methyl methylsulfinylmethyl sulfide to yield the corresponding 1,3-substituted derivative (8).

In step b, the sodium anion of (8) is reacted with the appropriate pyrimidine or pyridine derivative, such as 5-amino-4,6-dichloropyrimidine, followed by hydrolysis to give the corresponding ketone derivative (9).

In step c, the ketone derivative (9) is converted to the corresponding enol ether (10) by reacting (9) with the appropriate Wittig reagent, such as φ₃P=CH₂OCH₃ [methoxymethyl triphenylphosphylidine chloride], in the presence of n-butyllithium.

In step d, the enolate (10) is cyclized in the presence of acid, such as HCl, and the 3-hydroxy blocking group is removed according to standard techniques well known and appreciated in the art, to give the 6-substituted carbocyclic nucleoside analog (11).

In step e, the 6-substituted carbocyclic nucleoside analog (11) is modified to form the alkyl acylated or arylacyl derivative as described in Scheme A, step e, to yield the 9-substituted nucleoside derivative (1b). Where the 9-substituted carbocyclic nucleoside analog (11) bears a chlorine in the 6-position, the 6-chloro derivative can be converted to the 6-amino or 6-hydrogen derivative according to standard techniques well known and appreciated in the art.

The following example presents a typical synthesis as described by Scheme B. This example is understood to be illustrative only and is not intended to limit the scope of the invention in any way.

EXAMPLE 4

(1R,3R)-Trans-1-[9-(9-deazaadenyl)]3-hydroxycyclopentane hydrochloride

Step a:(1R,3R)-Trans-3-t-butyldimethylsilylox-1-[methyl (1-methylsulfinyl-1-methylsulfide)] cyclopentane To a stirring solution of methylsulfinylmethyl sulfide (1.2 equivalents) in THF at 0° C. add n-butyl lithium (1.2 equivalents) and allow to stir for 15 minutes. Over a 15 minute period, add dropwise a solution of (1S,3R)-Cis-1-methanesulfonyloxy-3-t-butyldimethylsilyloxy cyclopentane (1 equivalent) in THF and allow to stir for several hours at 0° C. to 25° C. Dilute the reaction with water and extract with ethyl acetate or methylene chloride. Wash the organic layer with water, brine, and dry over sodium sulfate. Concentrate the solution to dryness to yield the title compound as a crude product.

Step b: (1R,3R)-Trans-3-t-butyldimethylsilyloxy-1-[carbonyl(4-[5-amino-6-chloropyrimidine])] cyclopentane To a stirring solution of (1R,3R)-trans-3-t-butyldimethylsilyloxy-1-[methyl(1-methylsulfinyl-1-methylsulfide)] cyclopentane (1 equivalent) in THF at 0° C. add n-butyllithium and continue stirring for 15 minutes. Over a 15 minute period, add dropwise a solution of 5-amino-4,6-dichloropyrimidine (1.1 equivalents) in THF and stir the reaction mixture for 24 hours at room temperature. Dilute the reaction with water and extract with ethyl acetate or methylene chloride. Wash the organic layer with water, brine, and dry over sodium sulfate. Concentrate the solution to dryness to yield the title compound as a crude product. Purify the title compound using a silica gel column eluting with ethyl acetate/hexane.

Step c: (1R,3R)-Trans-3-t-butyldimethylsilyloxy-1-[ethylene-1-(4-[5-amino-6-chloropyrimidine])-2-methoxy] cyclopentane To a stirring suspension of methoxymethyl triphenylphosphylidine chloride (1.2 equivalents) in THF at 0° C. add n-butyllithium (1.2 equivalents) followed by stirring for 1 hour. Over a 15 minute period, add (1R,3R)-trans-3-t-butyldimethylsilyloxy-1-[carbonyl(4-[5-amino-6-chloropyrimidine])]cyclopentane (1 equivalent) in THF and stir overnight at 0° C. Concentrate the reaction mixture to dryness and dissolve the residue in diethyl ether. Cool to 0° C. for 1 hour and remove the precipitate (lithium chloride and triphenylphosphineoxide) by filtration. Concentrate the filtrate to yield the title compound. Purify the title compound using a silica gel column eluting with ethyl acetate/hexane.

Step d: (1R,3R)-trans-1-[9-(9-deazaadenyl)]-3-hydroxy cyclopentane Hydrochloride Dissolve (1R,3R)-trans-3-t-butyldimethylsilyloxy-1-[ethylene-1-(4-[5-amino-6-chloropyrimidine])-2-methoxy]-cyclopentane in aqueous methanol and a sufficient amount of 6N HCl and stir at room temperature for 4 hours. Neutralize the product with ammonium hydroxide and concentrate the reaction mixture to dryness to yield (1R,3R)-trans-3-t-butyldimethylsilyloxy-1-[9-(6-chloro-9-deazapurinyl)]cyclopentane. Purify the product using a silica gel column eluting with methylene chloride/ethanol. Enclose (1R,3R)-trans-3-t-butyldimethylsilyloxy-1-[9-(6-chloro-9-deazapurinyl)]cyclopentane in a sealed container of methanol and anhydrous ammonia for 24 hours applying heat if necessary. Remove the solvent and apply the product to a Dowex 50W™ column eluting with dilute ammonium hydroxide. Concentrate the eluant to dryness, take up in water, make acidic with 6N HCl and stir for 4 hours. Concentrate the solution to dryness to yield the title compound.

A general synthetic procedure for preparing compounds of formula (1) wherein $Y_9$ is a CH group and $Y_8$ is a nitrogen is set forth in Scheme C.

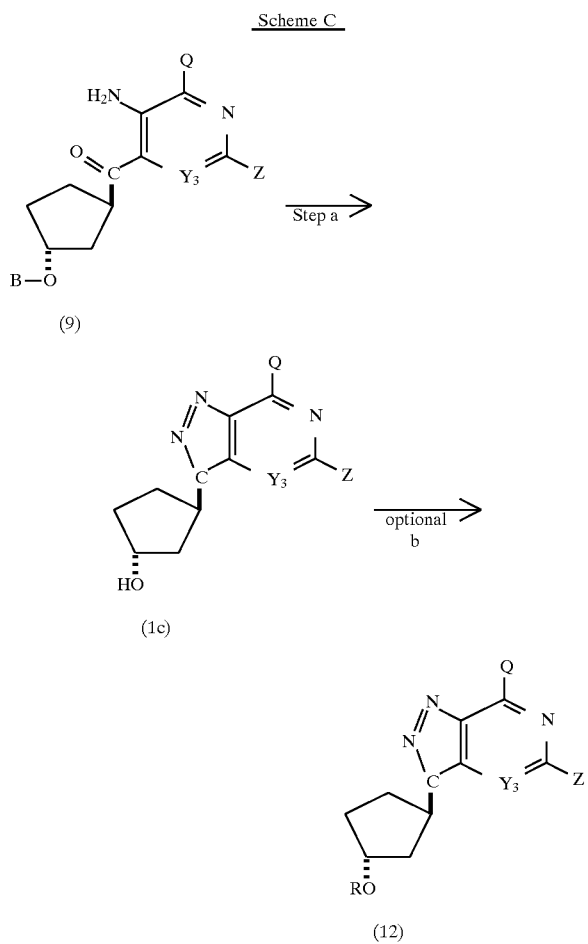

In step a, the ketone derivative (9), made as described in Scheme B, is converted to the corresponding oxime derivative and then cyclized to the corresponding 8-aza-9-deaza-6-substituted-nucleoside derivative by reacting the oxime with diethylazodicarboxylate (DEAD) and triphenylphosphine. In addition, the 3-hydroxy blocking group of (9) is removed according to standard techniques well known and appreciated in the art.

In step b, the 8-aza-9-deaza-6-substituted-nucleoside derivative can be converted to the corresponding 8-aza-9-deaza-6-substituted-nucleoside alkyl acyl or arylacyl derivative as described in Scheme A, step e. Where the 8-aza-9-deaza-6-substituted-carbocyclic-nucleoside derivative (1c) bears a chlorine in the 6-position, the 6-chloro derivative can be converted to the 6-amino or 6-hydrogen derivative according to standard techniques well known and appreciated in the art.

EXAMPLE 5

(1R,3R)-Trans-1-[9-(8-aza-9-deazaadenyl)]3-hydroxycyclopentane hydrochloride

Step a: (1R,3R)-trans-1-[9-(8-aza-9-deazaadenyl)]-3-hydroxy cyclopentane Hydrochloride To a solution of (1R,3R)-trans-3-t-butyldimethylsilyloxy-1-[carbonyl(4-[5-amino-6-chloropyrimidine])]-cyclopentane (1 equivalent) and hydroxylamine hydrochloride (1.2 equivalents) in dry methanol add a solution of sodium hydroxide (1.2 equivalents). After 2 hours add water and collect and dry the solid thus formed (oxime intermediate). Dissolve the oxime intermediate (1 equivalent) in methylene chloride followed by DEAD (1.2 equivalents) and triphenylphosphine (1.1 equivalents). Allow the mixture to react for 2 hours to yield (1R,3R)-Cis-3-t-butyldimethylsilyloxy-1-(9-[8-aza-6-chloro-9-deazapurinyl]) cyclopentane. Extract the reaction mixture with water and then brine. Dry the organic layer over sodium sulfate, concentrate to dryness and add diethyl ether to precipitate out the triphenylphosphine oxide. Remove the precipitate by filtration and purify the product on a silica gel column eluting with ethyl acetate/hexane.

Enclose (1R,3R)-trans-3-t-butyldimethylsilyloxy-1-(9-[8-aza-6-chloro-9-deazapurinyl])-cyclopentane in a sealed container of methanol and anhydrous ammonia for 24 hours applying heat if necessary. Remove the solvent and apply the product to a Dowex 50W™ column eluting with dilute ammonium hydroxide. Concentrate the eluant to dryness, take up in water, make acidic with 6N HCl and stir for 4 hours. Concentrate the solution to dryness to yield the title compound.

EXAMPLE 6

(1R,3R)-Trans-1-[9-(6-amino-2-cholopurinyl)]cyclopentan-3-ol hydrochloride

To a stirred solution of triphenyl phosphate (790 mg, 3.00 mmol) in dry THF (7 ml) at 0° C. was added diethyl azodicarboxylate (530 mg, 3.00 mmol) dropwise over a period of 15 minutes under $N_2$. The resulting orange-colored solution was allowed to stir for another 45 minutes at room temperature. The reaction mixture was then chilled to −78° C. and a solution of 2.6-dichloropurine (285 mg, 1.50 mmol) and (1S,3R)-cis-3-acetoxyclyclopentan-1-ol (144 mg, 1.00 mmol) in dry THF (3 ml) was added. The resulting solution was warmed to room temperature and stirred for 36 hours. The reaction mixture was concentrated and the residue was chromatographed on a silica gel column eluting with 2.5% methanol in methylene chloride to yield 515 mg of (1R,3R)-Trans-3-acetoxy-1-(9-(2,6-dicholopurinyl)] as a crude mixture.

A solution of (1R,3R)-Trans-3-acetoxy-1-[9-(2,6-dicholopurinyl)] (515 mg, crude) in anhydrous ethanol (15 ml) in a Diels-Alder tube was chilled to −78° C. under $N_2$. A rapid stream of $NH_3$ gas was passed through this solution for 5 minutes. The reaction tube was then sealed an the resulting solution was allowed to warm to room temperature and stirred for 15 hours at room temperature. The reaction mixture was concentrated and the residue was chromatographed on silic gel column eluting with 4% methaanol in methylene chloride to yield 300 mg reddish oil.

The reddish oil was taken up in methanol (5 ml). $K_2CO_3$ (200 mg, 1.45 mmol) was added and the resulting mixture was stirred for 5 hours. The reaction mixture was concentrated and the residue was chromatographed on a silica gel column eluting with 6% methanol in methylene chloride to yield 130 mg of (1R,3R)-Trans-1-[9-(6-amino-2-cholopurinyl)]cyclopentan-3-ol (51% overall yield) as a white solid. (1R,3R)-Trans-1-[9-(6-amino-2-cholopurinyl)]cyclopentan-3-ol was converted to a monohydrochloride salt: Optical Rotation D +9.828 (0.755 w/v%, MeOH); analysis for ($C_{10}H_{13}Cl_2N_5O$): C, 41.40; H, 4.48; N, 24.10; found C, 41.75; H, 4.37; N, 23.79.

EXAMPLE 7

Alkyl Acyl and Aryl Acyl Derivatives

Alkyl acyl and aryl acyl derivatives may be made from any of the above compounds. For example, (1R,3R)-trans-1-(9-adenyl)-3-hydroxycylopentane (1 mmol) is dissolved in pyridine (10 ml) and cooled to 0–5 C. Acyl acid chloride (1.1 mmol) is added dropwise and the reaction is stirred for 12 hours at room temperature. The reaction is diluted with $CH_2Cl_2$ and extracted with water, brine and concentrated to dryness. The material is purified on silica gel (20 g) eluting with 9:1 $CH_2Cl_2$/MeOH as a solvent system.

In general, where it is desired to synthesize the corresponding (1S,3S) enantiomer of the compounds of formula (1), procedures similar to those described above may be followed using the appropriate starting materials.

The present invention further provides a method of effecting immunosuppression, and more specifically, a method of suppressing adaptive immunity, in a patient in need thereof comprising administering to said patient an effective immunosuppressive amount of a compound of formula (1).

As used herein, the term "patient" refers to a warm-blooded animal such as a mammal which is suffering from a disease, such as an autoimmune disease or "graft versus host" disease, or is in danger of rejection of a transplanted allogeneic tissue or organ. It is understood that humans, mice and rats are included within the scope of the term "patient".

Administration of a compound of formula (1) to a patient results in an immunosuppressive effect in the patient. More specifically, administration of a compound of formula (1) to a patient results in suppression of adaptive immunity in the patient. In other words, by treatment of a patient with a compound of formula (1), the adaptive immune response of the patient is inhibited or suppressed over that present in the absence of treatment.

A patient is in need of treatment with an immunosuppressive agent, such as a compound of formula (1), where the patient is suffering from an autoimmune disease, "graft versus host" disease or in order to prevent rejection of transplanted allogeneic tissues or organs. The term "autoimmune disease" refers to those disease states and conditions wherein the immune response of the patient is directed against the patient's own constituents resulting in an undesirable and often terribly debilitating condition.

Patients suffering from autoimmune diseases such as rheumatoid arthritis, insulin-dependent diabetes mellitus, certain hemolytic anemias, rheumatic fever, thyroiditis, septic shock syndrome, ulcerative colitis, myestheniagravis, glomerulonephritis, allergic encephalomyelitis, continuing nerve and liver destruction which sometimes follows viral hepatitis, multiple sclerosis and systemic lupus erythematosus are in need of treatment with an immunosuppressive agent such as a compound of formula (1). Rheumatoid arthritis, insulin-dependent diabetes mellitus and multiple sclerosis are characterized as being the result of a cell-mediated autoimmune response and appear to be due to the action of T-cells. Myestheniagravis and systemic lupus erythematosus are characterized as being the result of a humoral autoimmune response. As such, treatment of patients suffering from these diseases by administration of a compound of formula (1) will be particularly effective in preventing further deterioration or worsening of the patient's condition. Treatment of a patient at an early stage of an autoimmune disease, such as rheumatoid arthritis, insulin-dependent diabetes mellitus, multiple sclerosis, myestheniagravis or systemic lupus erythematosus, would be particularly effective in preventing further deterioration of the disease state into a more serious condition. For example, insulin-dependent diabetes mellitus (IDDM) is an autoimmune disease which is believed to result from the autoimmune response directed against the β-cells of the islets of Langerhans which secrete insulin. Treatment of a patient suffering from an early stage of IDDM prior to the complete destruction of the β-cells of the islets of Langerhans would be particularly useful in preventing further progression of the disease since it would prevent or inhibit further destruction of remaining insulin-secreting β-cells. It is understood that treatment of a patient suffering from an early stage of other autoimmune diseases will also be particularly useful to prevent or inhibit further natural progression of the disease state to more serious stages.

Patients who have received or who are about to receive an allogeneic tissue or organ transplant, such as an allogeneic kidney, liver, heart, skin, bone marrow, are also patients who are in need of prophylactic treatment with an immunosuppressive agent such as a compound of formula (1). An immunosuppressive agent will prevent the adaptiveimmune response of the donee from rejecting the allogeneic tissue or organ of the donor. Likewise, patients suffering from "graft versus host" disease are patients who are in need of treatment with an immunosuppressive agent such as a compound of formula (1). An immunosuppressive agent will prevent the adaptive immune response of the transplanted tissue or organ from rejecting the allogeneic tissue or organ of the donee.

Based on standard clinical and laboratory tests and procedures, an attending diagnostician, as a person skilled in the art, can readily identify those patients who are in need of treatment with an immunosuppressive agent such as a compound of formula (1).

An effective immunosuppressive amount of a compound of formula (1) is that amount which is effective, upon single or multiple dose administration to a patient, in providing an immunosuppressive effect or, more particularly, a suppression of adaptive immune response. An immunosuppressive effect refers to the slowing, interrupting, inhibiting or preventing the further expression of the adaptive immune response.

An effective immunosuppressive amount of a compound of formula (1) can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

An effective immunosuppressive amount of a compound of formula (1) is expected to vary from about 0.1 milligram per kilogram of body weight per day (mg/kg/day) to about 500 mg/kg/day. Preferred amounts are expected to vary from about 1 to about 50 mg/kg/day.

In effecting treatment of a patient, a compound of formula (1) can be administered in any form or mode which makes the compound bioavailable in effective amounts, including oral and parenteral routes. For example, compounds of formula (1) can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In another embodiment, the present invention provides compositions comprising a compound of formula (1) in admixture or otherwise in association with one or more inert carriers. These compositions are useful, for example, as assay standards, as convenient means of making bulk shipments, or as pharmaceutical compositions. An assayable amount of a compound of formula (1) is an amount which is readily measurable by standard assay procedures and techniques as are well known and appreciated by those skilled in the art. Assayable amounts of a compound of formula (1) will generally vary from about 0.001% to about 75% of the composition by weight. Inert carriers can be any material which does not degrade or otherwise covalently react with a compound of formula (1). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective immunosuppressive amount of a compound of formula (1) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use, including topical use, and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, including topical administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possesses a particular generic utility, certain groups and configurations are preferred for compounds of formula (1) in their end-use application. Compounds of the formula (1) wherein $Y_3$ is nitrogen are generally preferred. Compounds of the formula (1) wherein $Y_5$ is nitrogen are generally preferred. Compounds of the formula (1) wherein $Y_7$ is nitrogen are generally preferred. Compounds of the formula (1) wherein $Y_8$ is a CH group are generally preferred. Compounds of the formula (1) wherein $Y_9$ is nitrogen are generally preferred. Furthermore, compounds of the formula (1) wherein Q is $NH_2$ and Z is hydrogen are generally preferred. Also preferred are compounds of the formula (1) wherein Q is $NH_2$ and Z is a halogen.

The following specific compounds of formula (1) are especially preferred:
(1R,3R)-Trans-1-(9-adenyl)-3-hydroxycyclopentane hydrochloride,
(1S,3S)-Trans-1-(9-adenyl)-3-hydroxycyclopentane hydrochloride, and
(1R,3R)-Trans-1[9-(6-amino-2-chloropurinyl)] cyclopentanol-3-ol hydrochloride.

Also preferred are compounds of formula (1) where Q is $NH_2$, Z is hydrogen and R is $C_1$ to $C_7$ alkyl acyl, such as where R is methyl, ethyl, propyl, isopropyl, butyl, isobutyl, tert-butyl, sec-butyl, pentyl, isopentyl, neopentyl, and the like. One skilled in the art would know how to make these based on the teachings in Example 1, step b, which exemplifies where R is methyl, (1R,3R)-trans-1-(9-adenyl)-3-acetoxycyclopentane and Example 7.

The following studies illustrate the utility of the compounds of formula (1). These studies are understood to be illustrative only and are not intended to limit the scope of the invention in any way. As used herein the following terms have the indicated meanings: "$\mu M$" refers to micromolar concentration; "Units" refers to the internationally accepted measurement of protein; "S.D." refers to standard deviation; "ηmol" refers to nanomoles; "ηg" refers to nanograms.

REGULATION OF MHC CLASS II EXPRESSION

Using the method of Edwards (*J. of Cell Biochemistry* 5E,155(1991)), the ability of a compound of formula (1) to reduce Major Histocompatibility complex (MHC) class II antigen levels on macrophages (Mφ) obtained from *M.tuberculosis*-treated rats may be measured. Cells obtained from treated rats are plated into tissue culture for a period of 4 hours to purify adherent cells, then treated with increasing levels of drug for a period of 18 hours. After this incubation period, cells are scraped from the dishes and stained using flow cytometry analysis with various monoclonal antibodies such as OX-6 a monoclonal antibody specific for MHC class II antigens and OX-42 a monoclonal antibody specific for rat macrophages. Data indicate (1R,3R)-Trans-1(9-Adenyl) cyclopentan-3-0l hydrochloride (10 $\mu M$) reduces the expression of MHC II antigen expression on rat macrophages in vitro by nearly 33% (39%OX-6/OX-42 double positive macrophages) compared to the positive control rat macrophages obtained from Tuberculosis-treated rats (59% OX-6/OX42 double positive macrophage cells).

REGULATION OF ANTIGEN PRESENTATION TO RAT T-CELL HYBRIDOMA

Using the method of Ku (*Cellular Immunology* 130, (1990)), and a Lewis (LEW/N) rat T-cell hybridoma reactive with the protein methylated bovine serum albumin (mBSA), the ability of a compound of formula (1) to regulate Mφ antigen presentation in vitro may be measured. Peritoneal macrophages obtained from LEW/N rats are plated into tissue culture and treated with 100 $\mu g$ of mBSA and drug. A control is prepared similarly. After a period of 18 hours the cells are washed and incubated with the T-cell hybridoma for an additional 12 hours. Supernatants from these cultures are obtained and measured for content of Interleukin-2, a T-cell derived lymphokine which is produced by activated T-cells. Data indicate (1R,3R)-Trans-1(9-Adenyl)cyclopentan-3-0l hydrochloride inhibits T-cell activation. Rat macrophage antigen presentation and the subsequent production of Interleukin-2 are inhibited when drug is administered over a concentration range from 0.1 to 100 $\mu M$ as illustrated in the following table.

| In Vitro Concentration | % Inhibition |
|---|---|
| 0.1 $\mu M$ | 7.6 |
| 1.0 $\mu M$ | 30.9 |
| 10.0 $\mu M$ | 48.7 |
| 100.0 $\mu M$ | 55.3 |

REGULATION OF ENDOTOXIN LETHALITY

Using the method of Silverstein, (*J. Exp. Med.* 173, 357 (1991)) a mouse endotoxin lethality model may be used to determine if a compound of formula (1) has the ability to inhibit endotoxin-induced septic shock which is dependent on the production of Tumor Necrosis Factor-α (TNF-α). CF1 mice pretreated at time (t)=−1hr with drug are challenged with 18 mg of D-glactoseamine and 50 ng of LPS, then observed for death over an 8–72 hour period. Data indicate (1R,3R)-Trans-1(9-Adenyl)cyclopentan-3-Ol hydrochloride (100 mg/kg i.p.) protects against endotoxin lethality.

INHIBITION OF TUMOR NECROSIS FACTOR ALPHA

Peripheral blood mononuclear cells (PBMC) are isolated from venous blood collected from healthy volunteers in sodium citrate (5 ml of 3.6% sodium citrate for 45 ml of blood) by density gradient centrifugation of 5 minutes at 1500 rpm. The PBMC are resuspended in about 10 ml of RPMI-1640 with antibiotics. Approximately $2 \times 10^6$ cells of PBMC are added to tissue culture plates, incubated for 45–60 minutes at 37° C. with 5% $CO_2$, aspirated, and washed twice by adding about 0.5 ml fresh RPMI-1640 with 10% non-mitogenic FBS (RPMI complete) and shaking for 15 to 30 seconds. 1.0 ml RPMI-1640 is added per well to the remaining adherent cells, which are pretreated with test compound solution about 15 minutes prior to endotoxin stimulation (1 $\mu g$/ml lipopolysaccharide from *E.coli* or solvent concentrations equal to those of test compounds.

Cultures are incubated for 18 hours t 37° C. in 5% CO2. Supernatants are tested from TNF-a using a commercial ELISA kit (Cistron, Pine Brook, N.J.). The $IC_{50}$ is determined using SOFTmax software program.

The $IC_{50}$ values for (±)-Trans-1-(9-adenyl)-2-hydroxycyclopentane (described in Lin U.S. Pat. No. 3,917, 837) is 22.2 $\mu M$; for (1R,3R)-Trans-1-(9-Adenyl) cyclopentan-3-Ol hydrochloride, 9 $\mu M$; and for (1R,3R)-Trans-1-[9-(6-amino-2-cholopurinyl)]cyclopentan-3-ol hydrochloride, 4.1 $\mu M$.

What is claimed is:
1. A compound of the formula

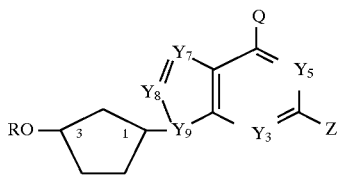

wherein
the substituent in the 3-position on the cyclopentanyl ring is in the TRANS configuration relative to the bicyclic substituent, $Y_3$, $Y_5$, $Y_7$, and $Y_9$ are each nitrogen and $Y_8$ is a CH group, R is a $C_1$–$C_7$ alkyl acyl or aryl acyl, Q is $NH_2$, halogen or hydrogen, and Z is hydrogen, halogen, or $NH_2$;

or a pharmaceutically-acceptable salt thereof.

2. A composition comprising a compound of claim 1 in admixture or otherwise in association with an inert carrier.

3. A pharmaceutical composition comprising a compound of claim 1 in admixture or otherwise in association with one or more pharmaceutically acceptable carriers or excipients.

4. A method of suppressing adaptive immunity in a patient in need thereof comprising administering to said patient an effective immunosuppressive amount of a compound of claim 1.

5. A method according to claim 4 wherein the patient is in need of treatment for an autoimmune disease.

6. A compound of claim 1 wherein R is a $C_1$–$C_6$ alkyl acyl.

7. A compound of claim 6 wherein the compound is (1R,3R)-Trans-1-(9-adenyl)-3-acetoxy-cyclopentane.

8. A compound of claim 6 wherein the compound is (1S,3S)-Trans-1-(9-adenyl)-3-acetoxy-cyclopentane.

9. A compound of claim 6 wherein the compound is (1R,3R)-trans-1-[9-(2,6-diamino)purine]-3-acetoxycyclopentane.

10. A compound of claim 1 wherein R is an aryl acyl.

11. A compound of claim 10 wherein R is (1R,3R)-Trans-1-(9-adenyl)-3-benzoyloxy-cyclopentane.

12. A compound of claim 10 wherein the compound is (1S,3S)-Trans-1(9-adenyl)-3-benzoyloxy-cyclopentane.

13. A method of effecting immunosuppression in a patient in need thereof comprising administering to said patient an effective immunosuppressive amount of a compound of claim 1.

14. A method according to claim 5 wherein the autoimmune disease is systemic lupus erythematosus.

15. A method according to claim 4 wherein the patient is in need of treatment for allograft rejection.

16. A method according to claim 5 wherein the autoimmune disease is myesthenia gravis.

17. A method according to claim 5 wherein the autoimmune disease is insulin-dependent diabetes mellitus.

18. A method according to claim 5 wherein the autoimmune disease is multiple sclerosis.

19. A method according to claim 5 wherein the autoimmune disease is rheumatoid arthritis.

* * * * *